United States Patent
Yun et al.

(10) Patent No.: US 10,703,974 B2
(45) Date of Patent: Jul. 7, 2020

(54) LIQUID CRYSTAL COMPOUND AND LIQUID CRYSTAL COMPOSITION

(71) Applicant: SHIJIAZHUANG CHENGZHI YONGHUA DISPLAY MATERIAL CO., LTD., Shijiazhuang, Hebei Prov. (CN)

(72) Inventors: Guoliang Yun, Shijiazhuang (CN); Ke-Lun Shu, Shijiazhuang (CN); Zhe Shao, Shijiazhuang (CN); Xing Zhang, Shijiazhuang (CN); Jianming Cheng, Shijiazhuang (CN); Limei Zhang, Shijiazhuang (CN)

(73) Assignee: SHIJIAHUANG CHENGZHI YONGHUA DISPLAY MATERIAL CO., LTD., Shijiazhuang (CN)

( * ) Notice: Subject to any disclaimer, the term of this patent is extended or adjusted under 35 U.S.C. 154(b) by 0 days.

(21) Appl. No.: 15/990,302

(22) Filed: May 25, 2018

(65) Prior Publication Data
US 2019/0055471 A1  Feb. 21, 2019

(30) Foreign Application Priority Data
Aug. 16, 2017  (CN) .......................... 2017 1 0704668

(51) Int. Cl.
| | | |
|---|---|---|
| G02F 1/1333 | (2006.01) | |
| C09K 19/20 | (2006.01) | |
| C07C 43/225 | (2006.01) | |
| C09K 19/30 | (2006.01) | |
| C09K 19/12 | (2006.01) | |
| C09K 19/34 | (2006.01) | |
| C09K 19/04 | (2006.01) | |

(52) U.S. Cl.
CPC ............ *C09K 19/20* (2013.01); *C07C 43/225* (2013.01); *C09K 19/3066* (2013.01); *C09K 2019/0444* (2013.01); *C09K 2019/0466* (2013.01); *C09K 2019/122* (2013.01); *C09K 2019/123* (2013.01); *C09K 2019/124* (2013.01); *C09K 2019/3009* (2013.01); *C09K 2019/3016* (2013.01); *C09K 2019/3019* (2013.01); *C09K 2019/3025* (2013.01); *C09K 2019/3027* (2013.01); *C09K 2019/3422* (2013.01)

(58) Field of Classification Search
CPC ................ C09K 19/20; C09K 19/3066; C09K 2019/0444; C09K 2019/0466; C09K 2019/122; C09K 2019/123; C09K 2019/124; C09K 2019/3009; C09K 2019/3016; C09K 2019/3019; C09K 2019/3025; C09K 2019/3027; C09K 2019/3422; G02F 1/1333; C07C 43/225
USPC ..................................................... 252/299.61
See application file for complete search history.

(56) References Cited

U.S. PATENT DOCUMENTS

| | | | | |
|---|---|---|---|---|
| 7,001,647 B2 * | 2/2006 | Shinano | ............... | C07D 239/04 |
| | | | | 252/299.61 |
| 9,512,360 B2 * | 12/2016 | Saito | ................... | C09K 19/3402 |

FOREIGN PATENT DOCUMENTS

| | | | | |
|---|---|---|---|---|
| CN | 102924243 A | | 2/2013 | |
| CN | 103756688 | * | 4/2014 | ............. C09K 19/44 |
| CN | 104531166 A | | 4/2015 | |

\* cited by examiner

*Primary Examiner* — Geraldina Visconti
(74) *Attorney, Agent, or Firm* — Muncy, Geissler, Olds & Lowe, PC

(57) ABSTRACT

Provided is a liquid crystal compound represented by formula I,

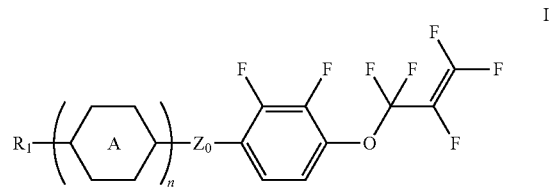

the compound having a positive dielectric anisotropy, a great elastic constant and a good solubility. Further provided is a liquid crystal composition comprising the liquid crystal compound represented by formula I, the liquid crystal composition having a good stability against light and heat, a lower viscosity, a wider refractive index that may be achieved by the adjustment of the monomer ratio, and a higher clearing point (a very wide service temperature range), and in particular, the liquid crystal composition has a higher light transmittance, thus allowing a display device to have a higher brightness or an energy saving effect.

10 Claims, No Drawings

LIQUID CRYSTAL COMPOUND AND LIQUID CRYSTAL COMPOSITION

TECHNICAL FIELD

The present invention belongs to the technical field of liquid crystal materials, and more particularly relates to a highly vertical dielectric positive liquid crystal compound, a liquid crystal composition, and a liquid crystal display device containing such a liquid crystal.

BACKGROUND ART

At present, the expansion of application range of liquid crystal compounds becomes larger and larger, and the liquid crystal compounds can be used in various types of displays, electro-optical devices, sensors, etc. There are a great variety of liquid crystal compounds used in the above-mentioned display field, wherein nematic liquid crystals are used most extensively. Nematic liquid crystals have been used in passive TN and STN matrix displays and systems having a TFT active matrix.

With regard to the application field of thin film transistor techniques (TFT-LCD), although the market in recent years has become very huge, and the techniques also become gradually mature, requirements of display techniques are increasing continuously, especially in terms of achieving a quick response, reducing the drive voltage for reducing power consumption, etc. Liquid crystal materials, as one of the important optoelectronic materials for liquid crystal displays, play an important role in improving the performance of a liquid crystal display.

As liquid crystal materials, they need to have good chemical and thermal stabilities and stabilities to electric fields and electromagnetic radiations. Moreover, as liquid crystal materials used for thin film transistor techniques (TFT-LCD), they not only need to have the stabilities as mentioned above, but also should have properties, such as a broader nematic phase temperature range, a suitable birefringence anisotropy, a very high electrical resistivity, a good ultraviolet resistant property, a high charge retention rate, a low vapour pressure, etc.

As for the application of dynamic picture displays, elimination of ghosting and trailing of display pictures, the liquid crystal is required to have a very fast response speed, and therefore the liquid crystal is required to have a lower rotary viscosity $\gamma_1$; in addition, for portable devices, the driving voltage of liquid crystal is desired to be as low as possible, in order to reduce the equipment energy consumption, and for displays for use in televisions, the requirements of drive voltage of the liquid crystals are not as low as that.

The viscosity, in particular rotary viscosity $\gamma_1$, of a liquid crystal compound directly affects the response time after the liquid crystal is energized, and both the rise time ($t_{on}$) and fall time ($t_{off}$) are proportional to the rotary viscosity $\gamma_1$ of the liquid crystal; moreover, since the rise time ($t_{on}$) is related to a liquid crystal cell and the drive voltage, it can be adjusted by means of increasing the drive voltage and reducing the thickness of the liquid crystal cell; while the fall time ($t_{off}$) is irrelevant to the drive voltage, but is mainly related to the elastic constant of the liquid crystal and the thickness of the liquid crystal cell, and thinning of cell thickness can result in a decrease in fall time ($t_{off}$); moreover, in different display modes, the movement manners of liquid crystal molecules are different, and the three modes TN, IPS and VA are inversely proportional to the mean elastic constant K, twist elastic constant and bend elastic constant, respectively.

After the introduction of a difluoromethyleneoxy linking group (—CF$_2$O—) into the liquid crystal molecule, the rotary viscosity $\gamma_1$ of the liquid crystal decreases. In addition, due to the contribution of the dipole moment of the difluoromethyleneoxy bridge (—CF$_2$O—), the dipole moment of the end group fluorine atom also increases to some extent, such that the dielectric anisotropy $\Delta\varepsilon$ of the liquid crystal molecule increases. Some liquid crystal compounds having a difluoromethyleneoxy linking group (—CF$_2$O—) having different substituents have been disclosed (CN 201210083535.0, CN 201410764634.4, etc.). However, the introduction of the —CF$_2$O— group can significantly reduce the clearing point of the liquid crystal.

According to the continuum theory of liquid crystal, a variety of different liquid crystals deformed under the action of an external force (an electric field, a magnetic field) can "rebound" back to the original shapes by intermolecular interactions; likewise, liquid crystals also form a "viscosity" due to the intermolecular force. Small changes of liquid crystal molecules may result in obvious changes in the conventional parameter performance of the liquid crystal, wherein for some of these changes, there is a certain rule, while for some changes, it is difficult to find a rule, which may also have obvious effects on the intermolecular interaction of the liquid crystal, these effects are very subtle, and to date, no perfect theoretical explanation has been formed yet.

The viscosity of a liquid crystal is related to the molecular structure of the liquid crystal, and studying the relationship between the viscosity of a liquid crystal system formed from different liquid crystal molecules and the molecular structures of the liquid crystals is one of important tasks of liquid crystal formulation engineers.

The reason why a liquid crystal display panel has a high energy consumption is that only about 5% of backlight can transmit through a display device and then be captured by human eyes, while most of the light is "wasted". If a liquid crystal having a high light transmittance can be developed, then the backlight intensity can be reduced, thereby achieving the purpose of saving energy consumption and extending the service time of a device.

The transmittance of the liquid crystal is directly related to the vertical dielectricity of the liquid crystal.

SUMMARY OF THE INVENTION

The present invention provides a novel liquid crystal compound represented by formula I, and such a compound has a positive dielectric anisotropy as well as a high vertical dielectricity, and has a good stability against light and heat, a lower viscosity, a wide refractive index that may be achieved by changing the structure, and a higher clearing point.

A liquid crystal compound provided by the present invention is

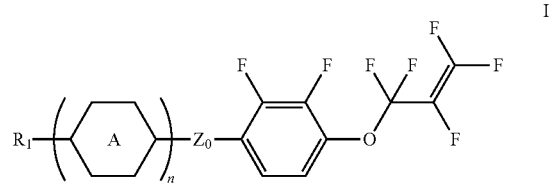

wherein $R_1$ represents an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any one or more non-connected $CH_2$ in group $R_1$ may be substituted with cyclopentyl, cyclobutyl, cyclopropyl or —O—;

each

independently represents

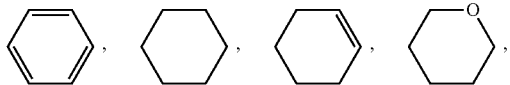

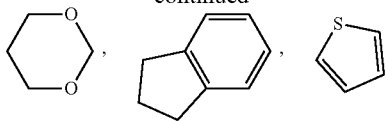

or fluorobenzene;

n represents 1, 2, 3 or 4; and $Z_0$ represents $CF_2O$, $CH_2O$, $COO$ or a single bond.

Where n represents 2 or 3, preferably not every

represents

.

The liquid crystal compound represented by formula I is preferably a compound represented by formulas I1 to I24:

I1

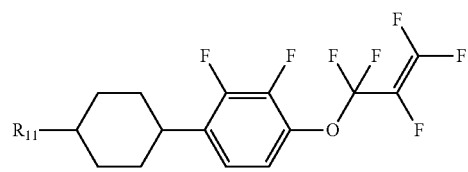

I2

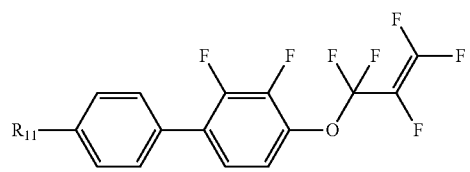

I3

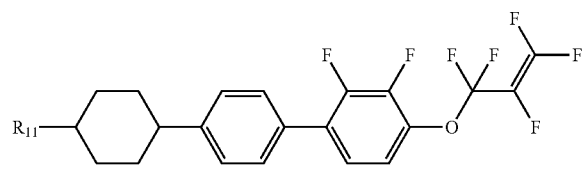

I4

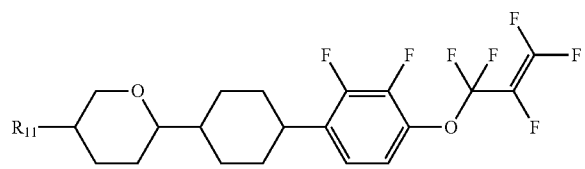

I5

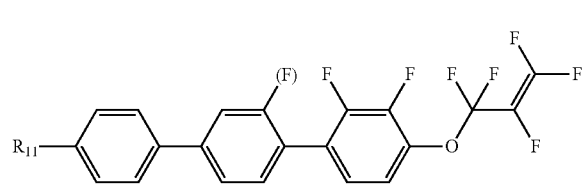

I6

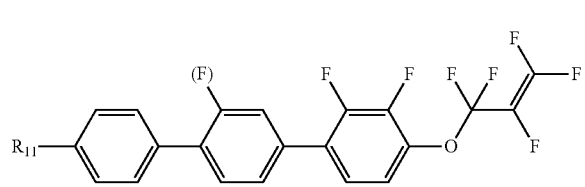

I7

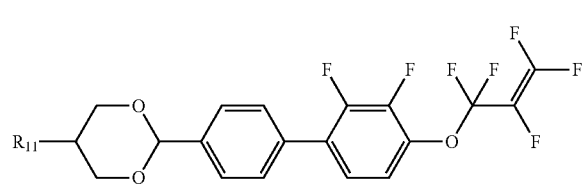

I8

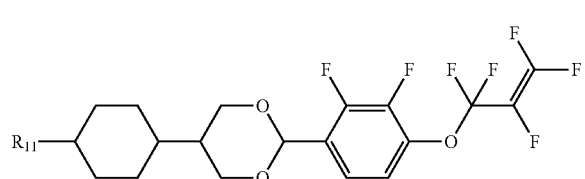

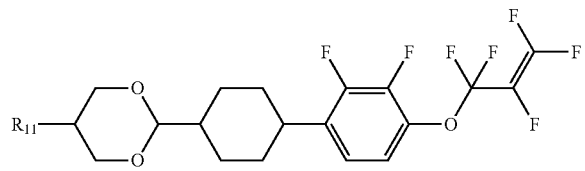 I9
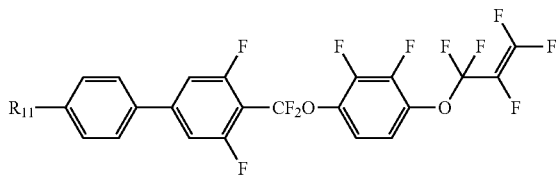 I10
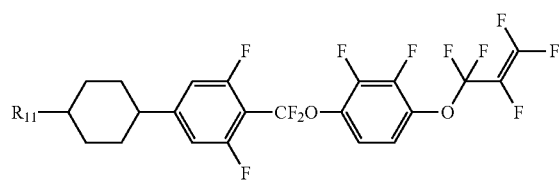 I11
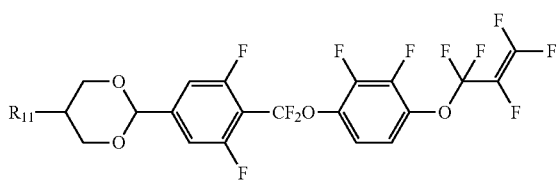 I12
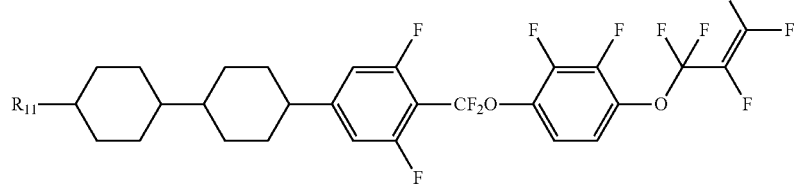 I13
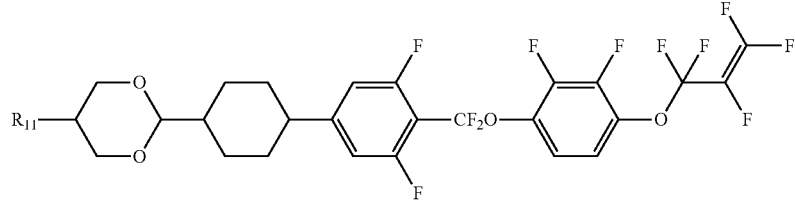 I14
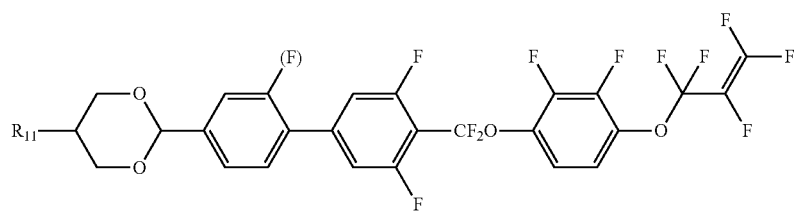 I15
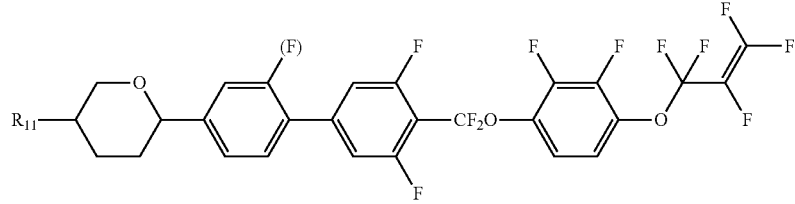 I16
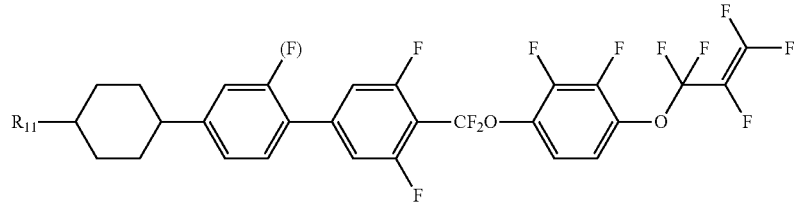 I17

-continued

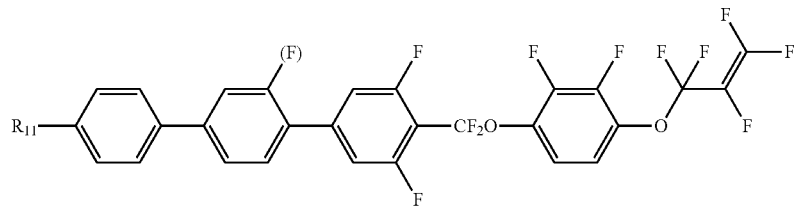
I18

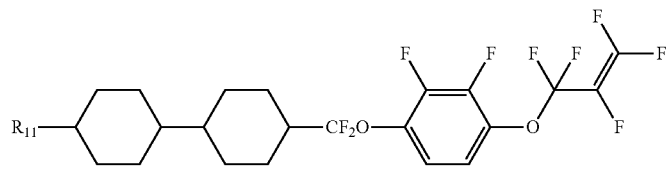
I19

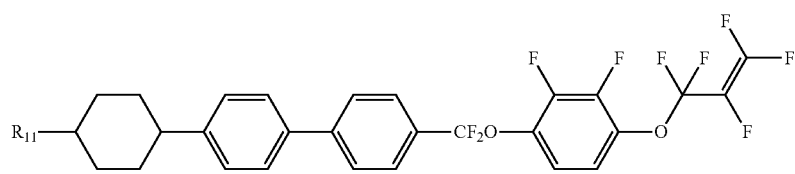
I20

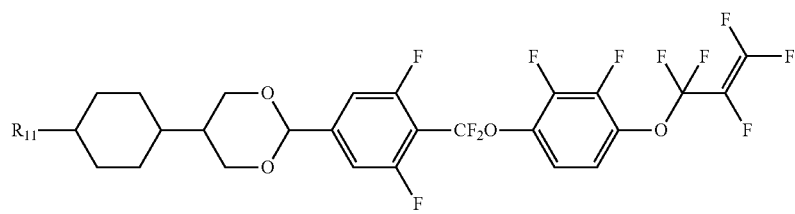
I21

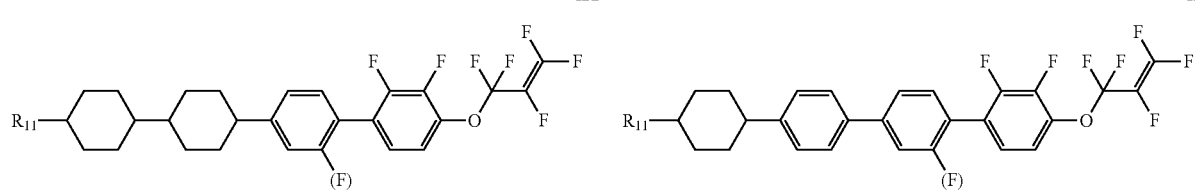
I22          I23

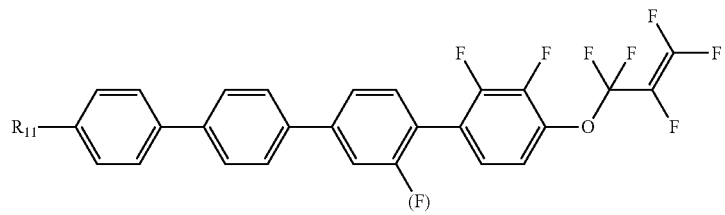
I24 wherein each $R_{11}$ independently represents an alkyl group having a carbon atom number of 1-6, cyclopentyl or cyclopropylmethyl; and each (F) independently represents F or H.

The compound represented by formula I has a positive dielectric anisotropy, a greater elastic constant and a good solubility.

The present invention further provides a liquid crystal composition, which has a good stability against light and heat, a lower viscosity, a wider refractive index that may be achieved by adjusting the monomer ratio, and a higher clearing point (a very wide service temperature range), and in particular, the liquid crystal composition has a higher light transmittance, thus allowing a display device to have a higher brightness or an energy saving effect.

The liquid crystal composition comprises one or more compounds represented by formula I and one or more compounds represented by formula II

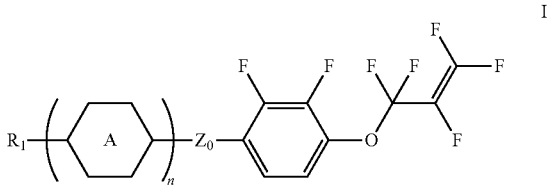
I

-continued

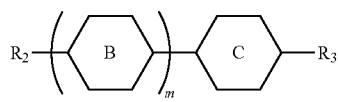
II

In the compound represented by formula II, $R_2$ and $R_3$ each independently represent an alkyl group having a carbon atom number of 1-10, an alkenyl group having a carbon atom number of 2-10, an alkoxy group having a carbon atom number of 1-10, and any one or more non-connected $CH_2$ in groups $R_2$ and $R_3$ may be substituted with cyclopentyl, cyclobutyl, cyclopropyl, or —O—;

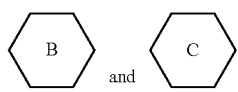

each independently represent

and m represents 1 or 2.

The compound of formula II is preferably a compound represented by formulas II1 to II17

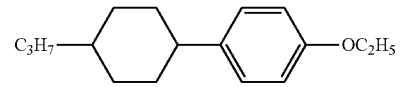
II-1

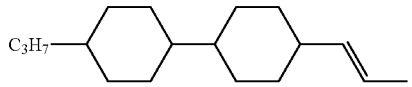
II-2

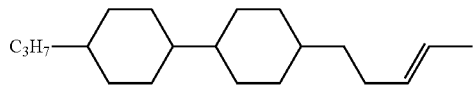
II-3

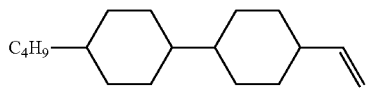
II-4

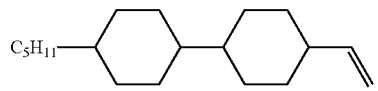
II-5

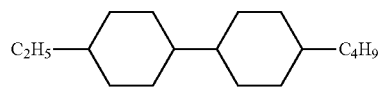
II-6

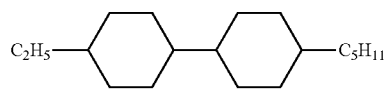
II-7

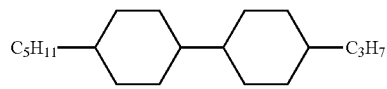
II-8

-continued

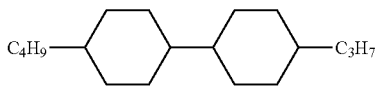
II-9

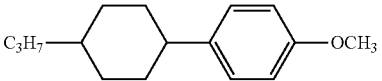
II-10

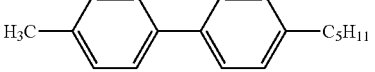
II-11

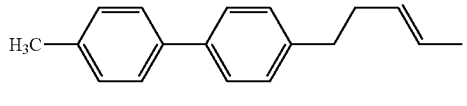
II-12

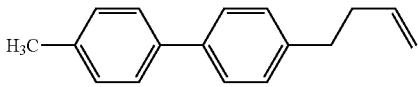
II-13

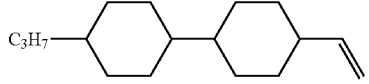
II-14

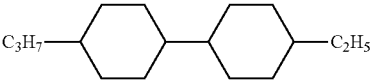
II-15

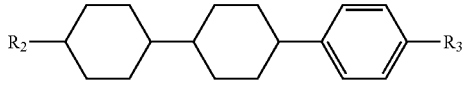
II-16

II-17 wherein $R_2$ and $R_3$ each independently represents an alkyl group having a carbon atom number of 1-10, an alkenyl group having a carbon atom number of 2-10, an alkoxy group having a carbon atom number of 1-10, and any one or more non-connected $CH_2$ in groups $R_2$ and $R_3$ may be substituted with cyclopentyl, cyclobutyl, cyclopropyl, or —O—.

In said liquid crystal composition, the total content in mass percentage of the compounds represented by formula I is preferably 1-40%, and further preferably 5-30%; and the total content in mass percentage of the compounds represented by formula II is preferably 5-65%, and further preferably 25-60%.

The compound represented by formula II generally has a lower viscosity and a lower refractive index, and the addition of such a component helps reduce the viscosity of the entire liquid crystal mixture.

Said liquid crystal composition may further comprise one or more compounds represented by formula III

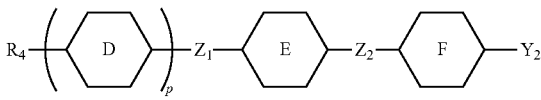
III wherein R₄ represents an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or an fluoro-substituted alkenoxy group having a carbon atom number of 3-8; and any one or more CH₂ in group R₄ may be substituted with cyclopentyl, cyclobutyl or cyclopropyl;

each independently represent:

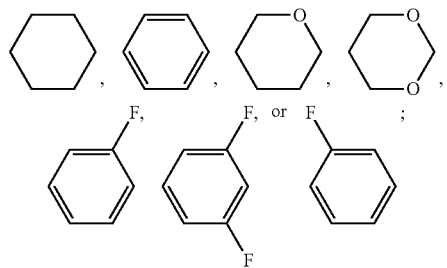

p represents 1, 2 or 3;

Z₁ and Z₂ each independently represent a single bond, —CF₂O—, —CH₂CH₂—, or —CH₂O—; and Y₂ represents F, a fluoro-substituted alkyl group having a carbon atom number of 1-5, a fluoro-substituted alkoxy group having a carbon atom number of 1-5, or an alkenyl group having a carbon atom number of 2-5.

The compound represented by formula III is preferably a compound represented by formulas III1 to III22

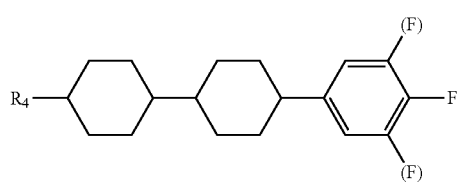
III1

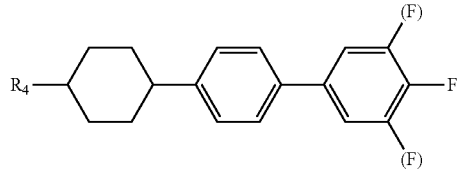
III2

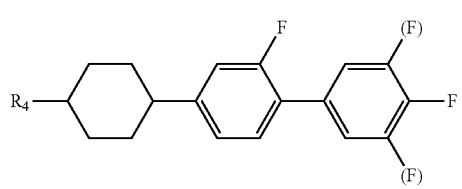
III3

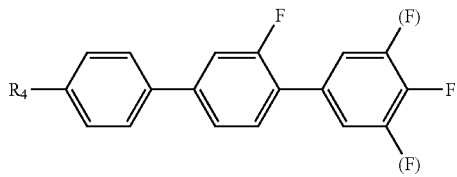
III4

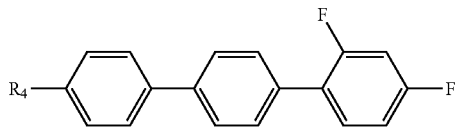
III5

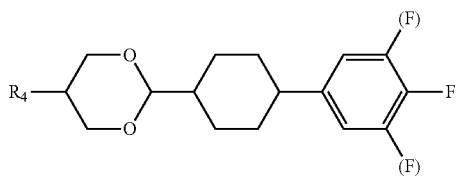
III6

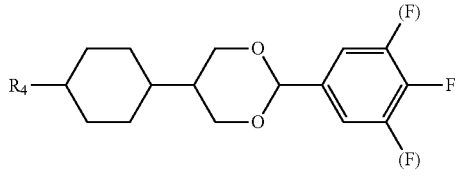
III7

III8

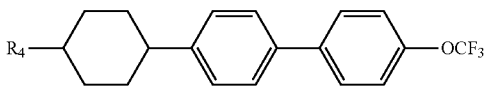
III9

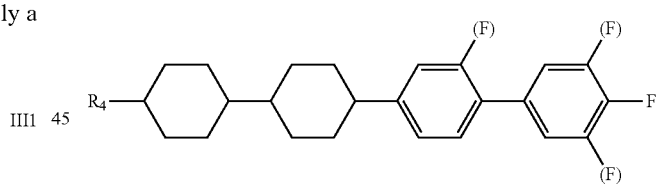
III10

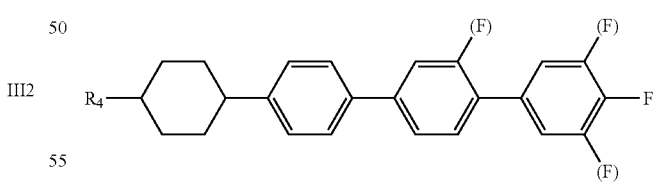
III11

III12

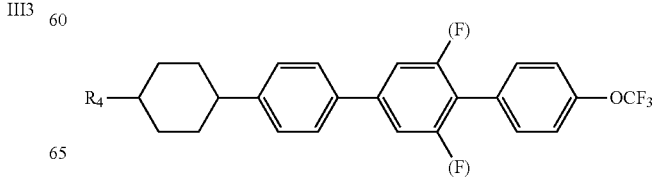

III13
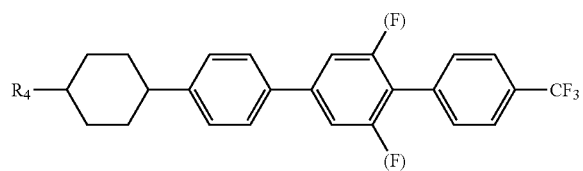

III14
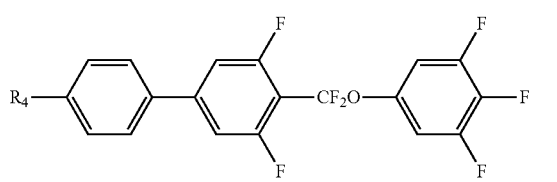

III15
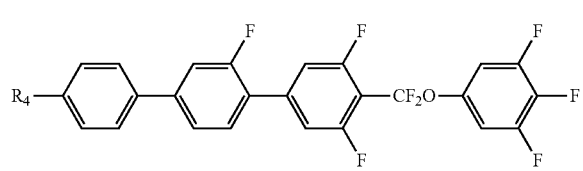

III16
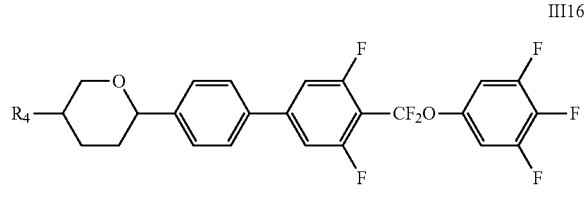

III17
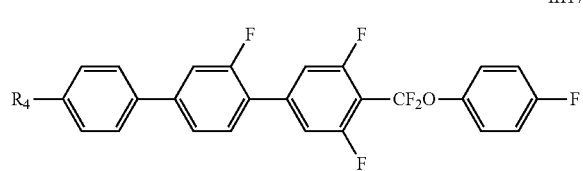

III18
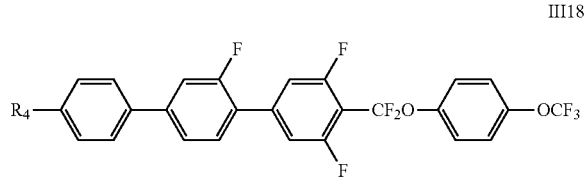

III19
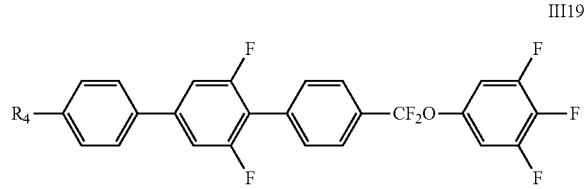

III20
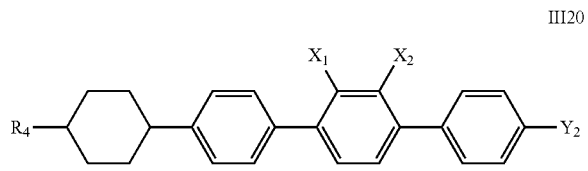

III21
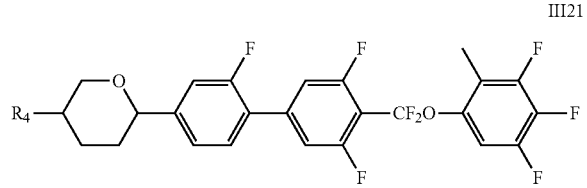

III22
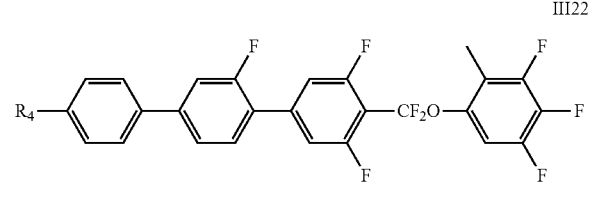

wherein $X_1$ and $X_2$ each independently represent H or F;

wherein each $R_4$ independently represents an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any $CH_2$ in group of $R_4$ may be substituted with cyclopentyl, cyclobutyl or cyclopropyl; (F) represents H or F; and $Y_2$ represents F, a fluoro-substituted alkyl group having a carbon atom number of 1-5, a fluoro-substituted alkoxy group having a carbon atom number of 1-5, or an alkenyl group having a carbon atom number of 2-5.

The addition of a compound represented by formula III can further adjust the dielectric anisotropy, refractive index, clearing point, elastic constant, viscosity, etc., of the liquid crystal mixture, and facilitates to widen the ranges of the parameters of the liquid crystal.

Said liquid crystal composition may further comprise one or more compounds represented by formula IV IV
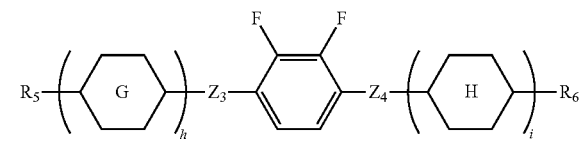

wherein $R_5$ and $R_6$ each independently represent an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any $CH_2$ in groups $R_5$ and $R_6$ may be substituted with cyclopentyl, cyclobutyl or cyclopropyl;

$Z_3$ and $Z_4$ each independently represent a single bond, —$CH_2CH_2$— or —$CH_2O$—;

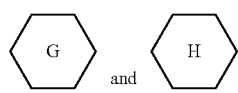

each independently represent

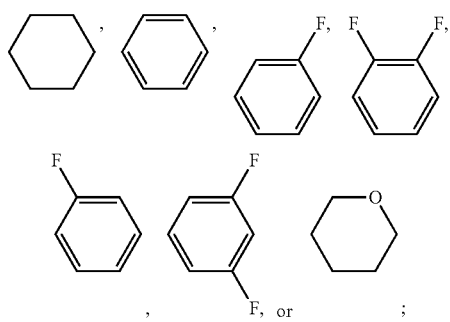

h represents 1, 2 or 3;
and i represents 0 or 1.

The compound represented by formula IV is preferably a compound of formulas IV-1 to IV-11

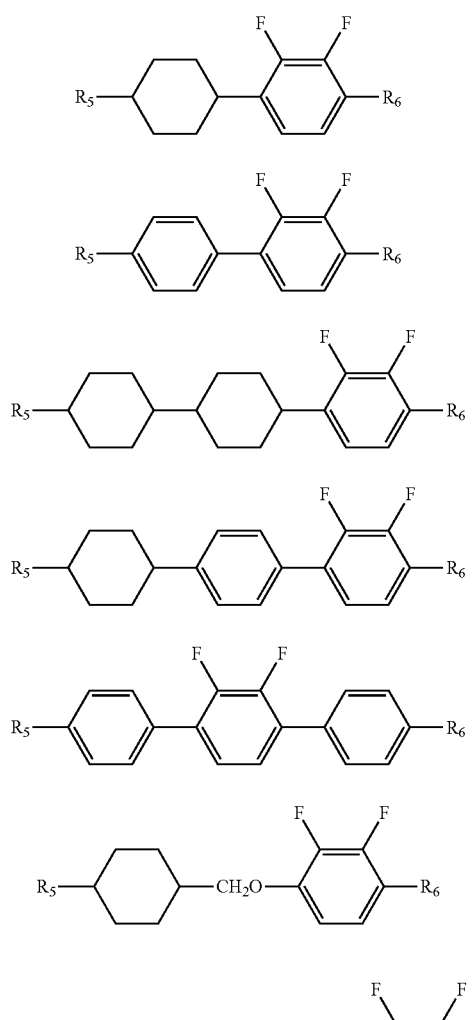

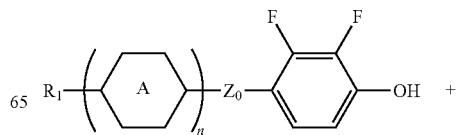

wherein $R_5$ and $R_6$ each independently represent an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any $CH_2$ in groups $R_5$ and $R_6$ may be substituted with cyclopentyl, cyclobutyl or cyclopropyl.

The addition of a compound represented by formula IV can further adjust the dielectric anisotropy, refractive index, clearing point, elastic constant, viscosity, etc., of the liquid crystal mixture, facilitates to widen the ranges of the parameters of the liquid crystal, and can further improve the vertical dielectricity of the liquid crystal.

The maximum addition amounts of the single monomers of formulas I, II, III, IV, V and VI are related to the number of rings, wherein the larger the number of rings, the poorer the solubility in general; and the solubility is also related to the end alkyl chains of a monomer, wherein the solubility of a monomer with alkyl is generally greater than that of a monomer with alkoxy, and by contrast when the carbon atom number is 1-5, the greater the carbon atom number, the better the solubility in general.

Each monomer has a different performance, and these monomers are used to adjust the various parameters of a liquid crystal, so that the liquid crystal is adaptive to the needs of liquid crystal display devices of different specifications.

Synthetic Route:

-continued

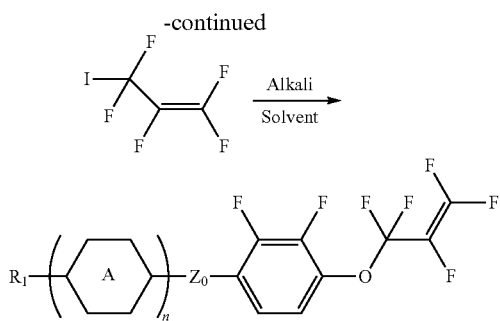

Alkali: the alkali can be sodium hydroxide, potassium hydroxide, sodium carbonate, sodium bicarbonate, potassium carbonate, sodium hydride, etc.;

Solvent: the solvent may be THF, DMF, acetone, etc.

The liquid crystal compound of formula I has a greater dielectric anisotropy in the liquid crystal molecule major axis parallel direction and vertical direction, with the dielectric anisotropy in the major axis parallel direction being greater than that in the vertical direction, and the overall anisotropy is exhibited positive; furthermore, the liquid crystal compound has the advantages of a higher clearing point CP, a good stability against light and heat, a greater elastic constant, particularly $K_{33}$, etc.

The present invention further relates to a liquid crystal display element or liquid crystal display comprising a compound of formula I and a liquid crystal composition formed by the combination of formulas I, II, III, IV, V and VI, and said liquid crystal display element or liquid crystal display is an active matrix display element or display or a passive matrix display element or display.

The display element or display may be of a TN, ECB, VA, IPS, FFS, PS-TN, PS-VA, PS-IPS, PS-FFS mode, etc.

DETAILED DESCRIPTION OF THE DRAWINGS

The present invention is further described as below in combination with particular embodiments, but the present invention is not limited to the following embodiments. Said methods are all conventional methods, unless otherwise specified. Said raw materials, unless otherwise specified, are commercially available.

The reaction process is generally monitored through TLC, and the post-treatments after the reaction is completed are generally water washing, extracting, combining organic phases and then drying, evaporating and removing the solvent under a reduced pressure, recrystallization and column chromatographic separation; and a person skilled in the art would be able to achieve the present invention according to the following description.

In the present specification, the percentages are mass percentages, the temperatures are in degree Celsius (° C.), and the specific meanings of other symbols and the test conditions are as follows:

Cp represents the clearing point (° C.) of the liquid crystal measured by a DSC quantitative method;

Δn represents the optical anisotropy, $n_o$ is the refractive index of an ordinary light, $n_e$ is the refractive index of an extraordinary light, the test condition is 25±2° C. and 589 nm, and an abbe refractometer is used for the test;

Δε represents the dielectric anisotropy, $\Delta\varepsilon = \varepsilon_{//} - \varepsilon_\perp$, wherein $\varepsilon_{//}$ is a dielectric constant parallel to a molecular axis, and $\varepsilon_\perp$ is a dielectric constant perpendicular to the molecular axis, the test condition is 25±0.5° C., a 20 micron parallel cell is used, and INSTEC: ALCT-IR1 is used for the test;

γ1 represents a rotary viscosity (mPa·s), the test condition is 25±0.5° C., a 20 micron parallel cell is used, and INSTEC: ALCT-IR1 is used for the test; and T (%) represents a transmittance, T (%)=100%*bright state (Vop) luminance/light source luminance, the test device is DMS501, the test condition is 25±0.5° C., the test cell is a 3.3 micron IPS test cell, both the electrode spacing and the electrode width are 10 microns, and the included angle between the frictional direction and the electrode is 10°; therefore, there is a positive correlation between a $\varepsilon_\perp$ and T, so in the evaluation of the transmittance, $\varepsilon_\perp$ can be used as an evaluation index for indication.

In the examples of the present invention application, liquid crystal monomer structures are represented by codes, wherein the code representation of cyclic structures, end groups and linking groups of the liquid crystals are shown in tables (I) and (II) below

TABLE (I)

Corresponding code for ring structure

| Cyclic structure | Corresponding code |
|---|---|
| (cyclohexane) | C |
| (benzene) | P |
| (monofluorobenzene) | G |
| (difluorobenzene, 2,3-F) | U |
| (difluorobenzene, other) | Gi |
| (difluorobenzene) | Y |
| (tetrahydropyran, O up) | A |
| (dioxane) | D |

TABLE (II)

| End groups and linking groups | Corresponding code |
|---|---|
| $C_nH_{2n+1}-$ | n |
| $C_nH_{2n+1}O-$ | nO |
| $-OCF_3$ | OT |
| $-CF_2O-$ | Q |
| $-F$ | F |
| $-CH_2CH_2-$ | E |
| $-CH=CH-$ | V |
| $-CH_2O-$ | O |
| $-CH=CH-C_nH_{2n+1}$ | Vn |
| 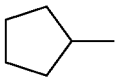 | C(5) |
| 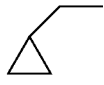 | C(3)1 |
| 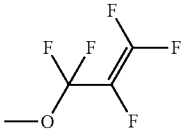 | O5FA |

For example:

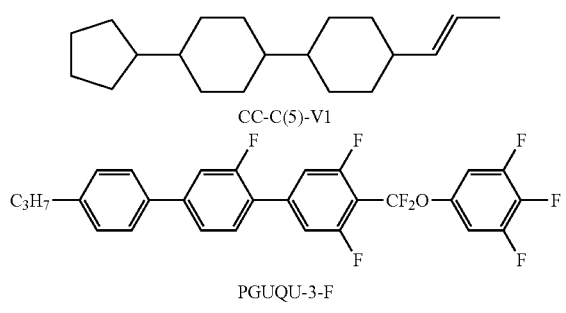

CC-C(5)-V1

PGUQU-3-F

Example 1

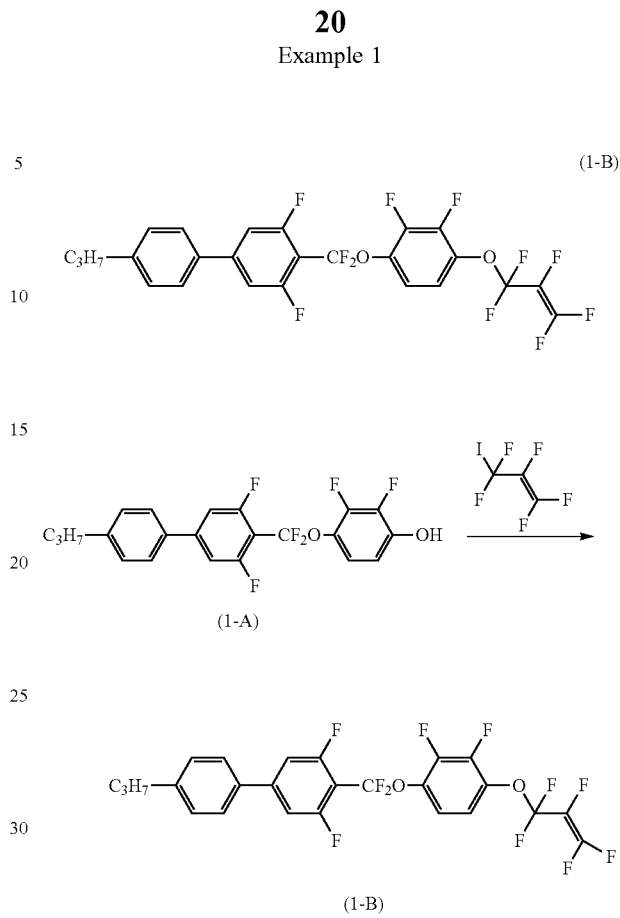

To a 250 ml three-necked flask, 4.26 g of (1-A), 30 ml of DMF and 0.6 g of sodium hydroxide are added, and reacted with stirring at room temperature for 20 minutes, a solution of 2.82 g of 1,1,2,3,3-pentafluoro-3-iodopropene in 10 ml of DMF is dropwise added at room temperature, and a reaction is carried out for 12 hours.

100 ml of water is added, the aqueous phase is extracted with petroleum ether, the organic phase is washed with water and passes through a silica gel column, and the chromatographic solution is concentrated to 10 ml and crystallises at a low temperature to obtain 3.33 g of a white crystal (1-B) with a yield of 60% and a GC of 99.92%.

Δε [1 KHz, 20° C.]: 11
$\varepsilon_\perp$: 8.7
Δn [589 nm, 20° C.]: 0.144
Cp: 55° C.

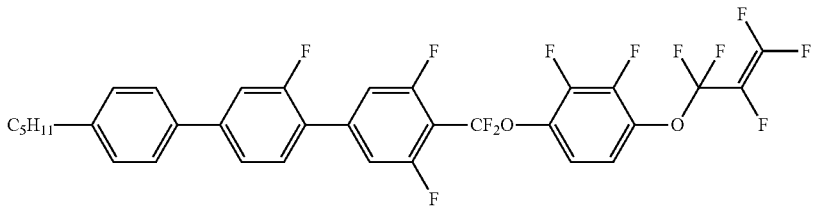

Δε[1 KHz, 20° C.]: 13
$\varepsilon_\perp$: 8.0
Δn [589 nm, 20° C.]: 0.200
Cp: 114° C.

Comparative parameters

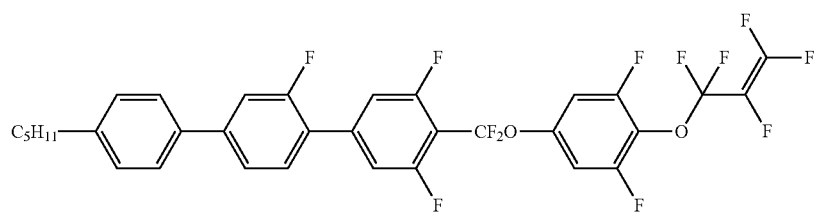

Δε[1 KHz, 20° C.]: 22
$\varepsilon_\perp$: 5.0
Δn [589 nm, 20° C.]: 0.198
Cp: 114° C.
The $\varepsilon_\perp$ of the comparative compound is significantly reduced

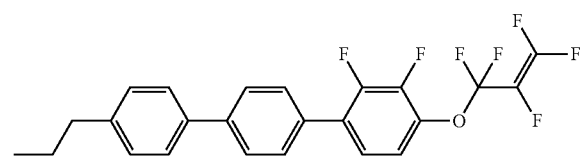 [SMILES: CCCc1ccc(-c2ccc(-c3ccc(OC(F)(F)C(F)=C(F)F)c(F)c3F)cc2)cc1]

Δε [1 KHz, 20° C.]: 4.0
$\varepsilon_\perp$: 5.5
Δn [589 nm, 20° C.]: 0.220
Cp: 135° C.
Comparative parameters:

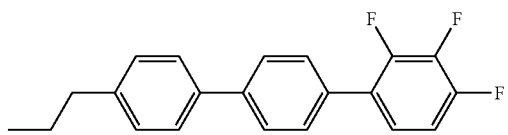 [SMILES: CCCc1ccc(-c2ccc(-c3ccc(F)c(F)c3F)cc2)cc1]

Δε [1 KHz, 20° C.]: 4.4
$\varepsilon_\perp$: 5.5
Δn [589 nm, 20° C.]: 0.220
Cp: 105° C.
The CP of the comparative compound is significantly reduced Example 2

| Classification | Liquid crystal monomer code | Content (%) |
| --- | --- | --- |
| II | CC-3-V | 50 |
| II | CCP-V-1 | 10 |
| II | CCP-V2-1 | 8 |
| I | PUQY-3-O5FA | 9 |
| I | PGUQY-3-O5FA | 6 |
| I | CCQY-5-O5FA | 7 |
| I | CPY-5-O5FA | 2 |
| I | AGUQY-3-O5FA | 8 |

Δε [1 KHz, 20° C.]: 4.3
$\varepsilon_\perp$: 4.2
Δn [589 nm, 20° C.]: 0.098
Cp: 95° C.
$\gamma_1$: 56 mPa · s.

Comparative Example 1

| Classification | Liquid crystal monomer code | Content (%) |
| --- | --- | --- |
| II | CC-3-V | 50 |
| II | CCP-V-1 | 10 |
| II | CCP-V2-1 | 8 |
|  | PUQU-3-O5FA | 9 |
|  | PGUQU-3-O5FA | 6 |
|  | CCQU-5-O5FA | 7 |
|  | CPU-5-O5FA | 2 |
|  | AGUQU-3-O5FA | 8 |

Δε [1 KHz, 20° C.]: 5.8
$\varepsilon_\perp$: 3.2
Δn [589 nm, 20° C.]: 0.090
Cp: 85° C.
$\gamma_1$: 55 mPa · s.

The $\varepsilon_\perp$ of the comparative example is remarkably reduced, and the transmittance thereof is reduced by 4%.

Example 3

| Classification | Liquid crystal monomer code | Content (%) |
| --- | --- | --- |
| II | CC-3-V | 33 |
| II | BCH-3-2 | 4 |
| I | PUQY-3-O5FA | 3 |
| I | PGUQY-3-O5FA | 6 |
| I | APUQY-3-O5FA | 6 |
| III | CCP-3-OT | 14 |
| III | PUQU-C(5)-F | 6 |
| III | PGUQU-C(3)-F | 7 |
| III | PGP-C(3)1-2 | 10 |
| III | CPUP-3-OT | 5 |
| III | PPGU-C(5)-F | 1 |
| IV | CPY-3-O2 | 5 |

Δε [1 KHz, 20° C.]: 5.2
$\varepsilon_\perp$: 3.9
Δn [589 nm, 20° C.]: 0.108
Cp: 76° C.
$\gamma_1$: 89 mPa · s.

Example 4

| Classification | Liquid crystal monomer code | Content (%) |
| --- | --- | --- |
| II | CC-3-V | 33 |
| II | CCP-V-1 | 7 |
| I | PUQY-3-O5FA | 3 |
| I | PGUQY-3-O5FA | 6 |
| I | CPUQY-3-O5FA | 6 |
| III | CCP-3-OT | 14 |
| III | PUQU-C(5)-F | 6 |

-continued

| Classification | Liquid crystal monomer code | Content (%) |
|---|---|---|
| III | PGUQU-C(5)-F | 7 |
| III | PGP-C(3)1-2 | 5 |
| III | PPGi-3-F | 5 |
| III | CPUP-3-OT | 4 |
| III | PPGU-C(5)-F | 1 |
| IV | CCY-3-O2 | 3 |

Δε [1 KHz, 20° C.]: 5.2
ε⊥: 3.7
Δn [589 nm, 20° C.]: 0.109
Cp: 79° C.
$\gamma_1$: 81 mPa · s.

Example 5

| Classification | Liquid crystal monomer code | Content (%) |
|---|---|---|
| II | CC-3-V | 40 |
| II | CC-3-V1 | 5 |
| I | PUQY-3-O5FA | 11 |
| I | PGUQY-3-O5FA | 6 |
| I | APUQY-3-O5FA | 6 |
| III | CCU-3-F | 11 |
| III | PUQU-C(5)-F | 6 |
| III | APUQU-C(5)-F | 4 |
| III | CPUQU-C(5)-F | 1 |
| III | CCPU-3-F | 4 |
| III | DUQU-C(5)-F | 1 |
| IV | CPY-3-O2 | 5 |

Δε [1 KHz, 20° C.]: 7.5
ε⊥: 4.2
Δn [589 nm, 20° C.]: 0.100
Cp: 77° C.
$\gamma_1$: 91 mPa · s.

Example 6

| Classification | Liquid crystal monomer code | Content (%) |
|---|---|---|
| II | CC-3-V | 30 |
| II | CP-3O2 | 2 |
| I | PUQY-3-O5FA | 3 |
| I | PGUQY-3-O5FA | 6 |
| I | DGUQY-3-O5FA | 6 |
| III | CPP-3-F | 14 |
| III | PUQU-C(5)-F | 6 |
| III | PGUQU-C(3)-F | 7 |
| III | PGP-3-F | 10 |
| III | CCGU-3-F | 5 |
| III | PPGU-C(5)-F | 1 |
| IV | CPY-3-O2 | 5 |

Δε [1 KHz, 20° C.]: 8.8
ε⊥: 3.9
Δn [589 nm, 20° C.]: 0.108
Cp: 76° C.
$\gamma_1$: 85 mPa · s.

The present invention is very suitable for displays of positive IPS and FFS modes. The liquid crystal composition of the present invention has a good stability against light and heat, a lower viscosity, a wider refractive index that may be achieved by adjustment, and a higher clearing point (a very wide service temperature range), and in particular, the liquid crystal composition has a higher light transmittance, thus allowing a display device to have a higher brightness or an energy saving effect.

The invention claimed is:
1. A liquid crystal compound represented by formula I,

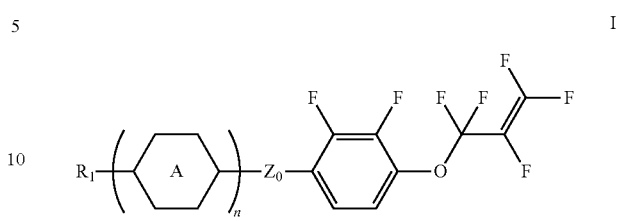

wherein $R_1$ represents an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any one or more non-connected $CH_2$ in the groups represented by $R_1$ may be substituted with cyclopentyl, cyclobutyl, cyclopropyl or —O—;

each

independently represents

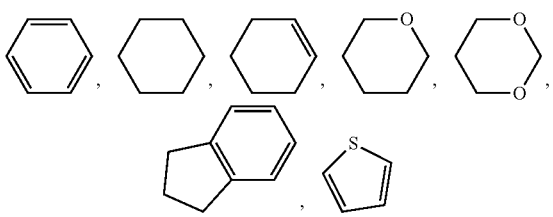

or fluorobenzene;
where n represents 2 or 3, not every

represents

.

$Z_0$ represents $CF_2O$, $CH_2O$, COO or a single bond; and, the dielectric anisotropy of the liquid crystal compound is positive.

2. The liquid crystal compound according to claim 1, wherein the liquid crystal compound represented by formula I is a compound represented by formulas I1 to I24;

I1
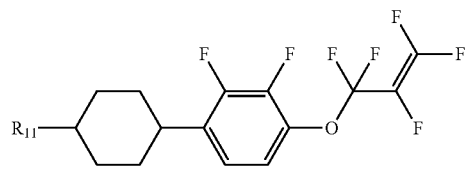
I2
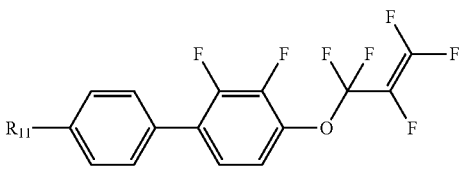
I3
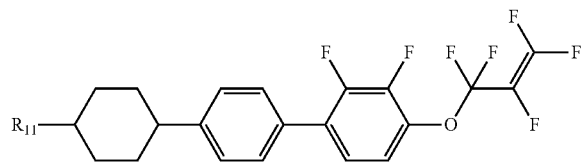
I4
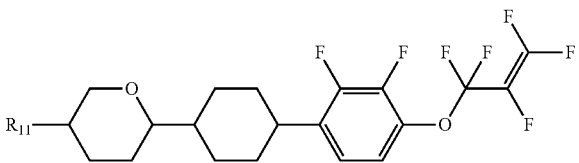
I5
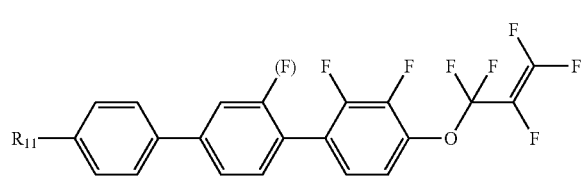
I6
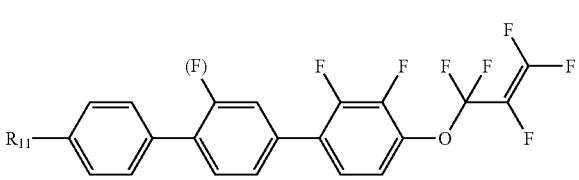
I7
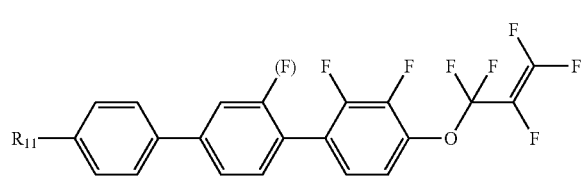
I8
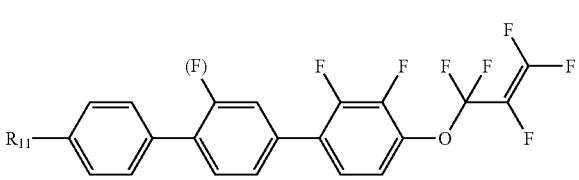
I9
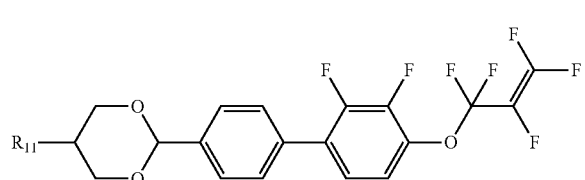
I10
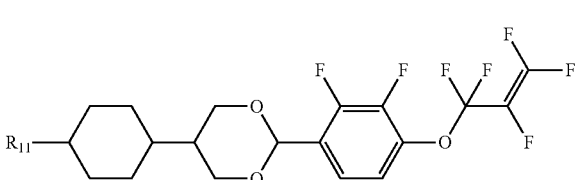
I11
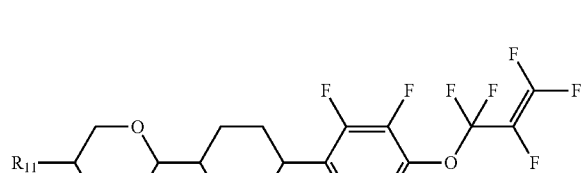
I12
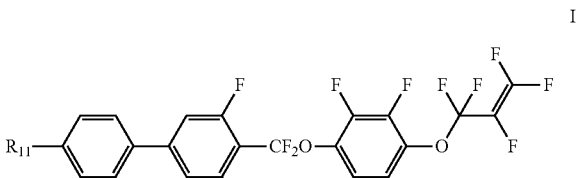
I13
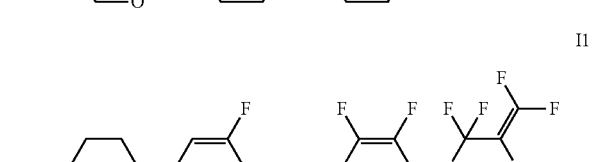
I14
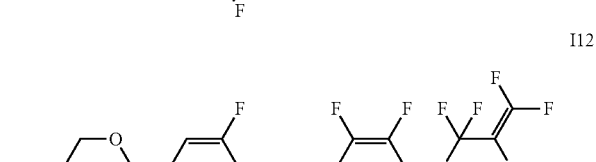

-continued
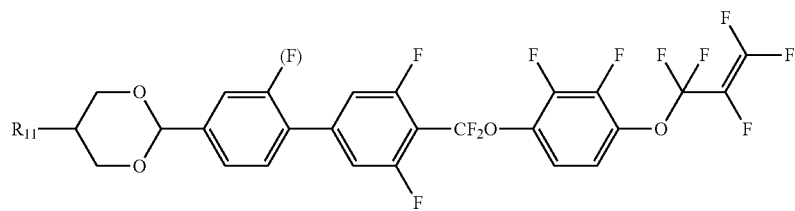
I15
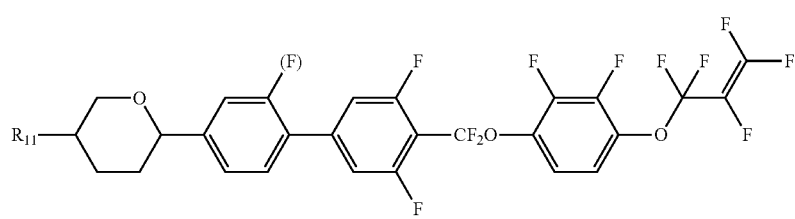
I16
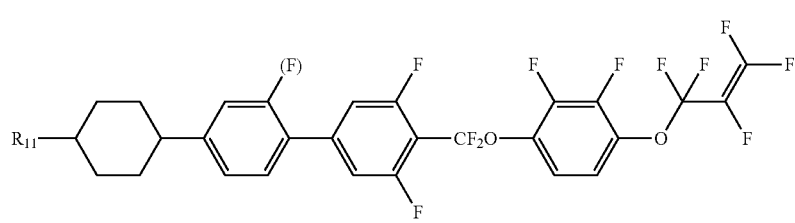
I17
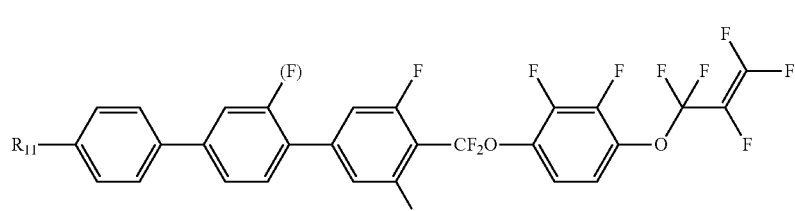
I18
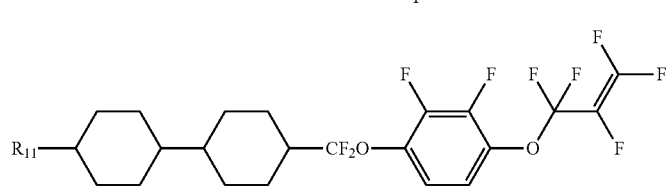
I19
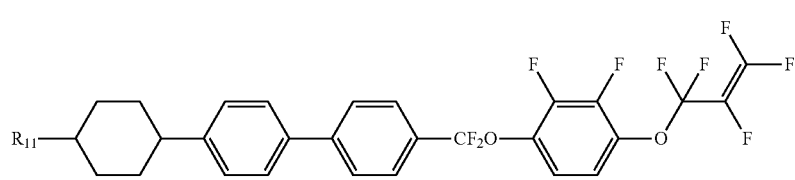
I20
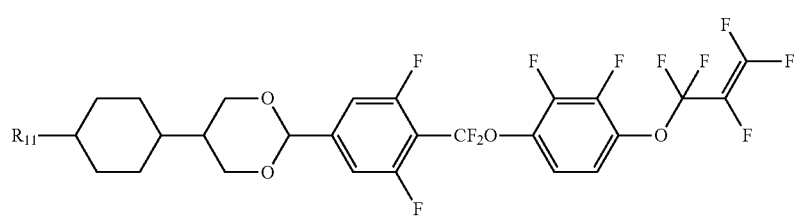
I21
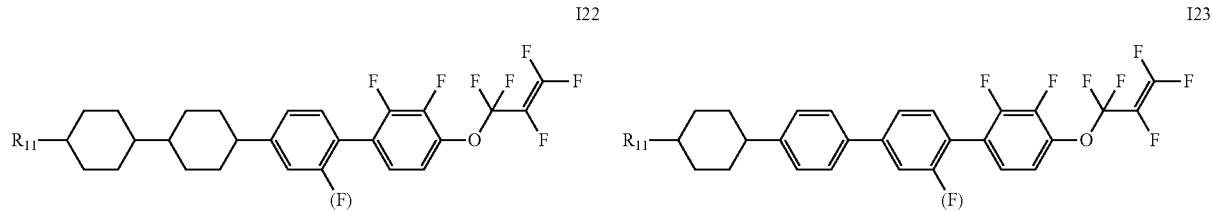
I22    I23

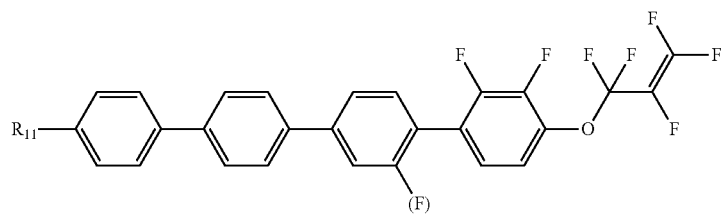

wherein each $R_{11}$ independently represents an alkyl group having a carbon atom number of 1-6, cyclopentyl or cyclopropylmethyl; and
each (F) independently represents F or H.

3. A liquid crystal composition, wherein said liquid crystal composition comprises one or more compounds represented by formula I of claim 1 and one or more compounds represented by formula II

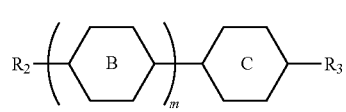

wherein $R_2$ and $R_3$ each independently represent an alkyl group having a carbon atom number of 1-10, an alkenyl group having a carbon atom number of 2-10, an alkoxy group having a carbon atom number of 1-10, and any one or more non-connected $CH_2$ in groups $R_2$ and $R_3$ may be substituted with cyclopentyl, cyclobutyl, cyclopropyl, or —O—;

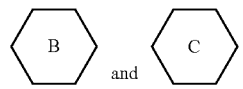

each independently represent

and m represents 1 or 2.

4. The liquid crystal composition according to claim 3, wherein said compound represented by formula II is a compound represented by formulas II1 to II17

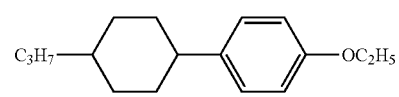

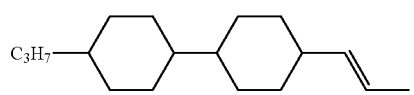

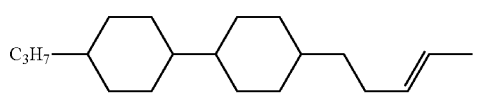

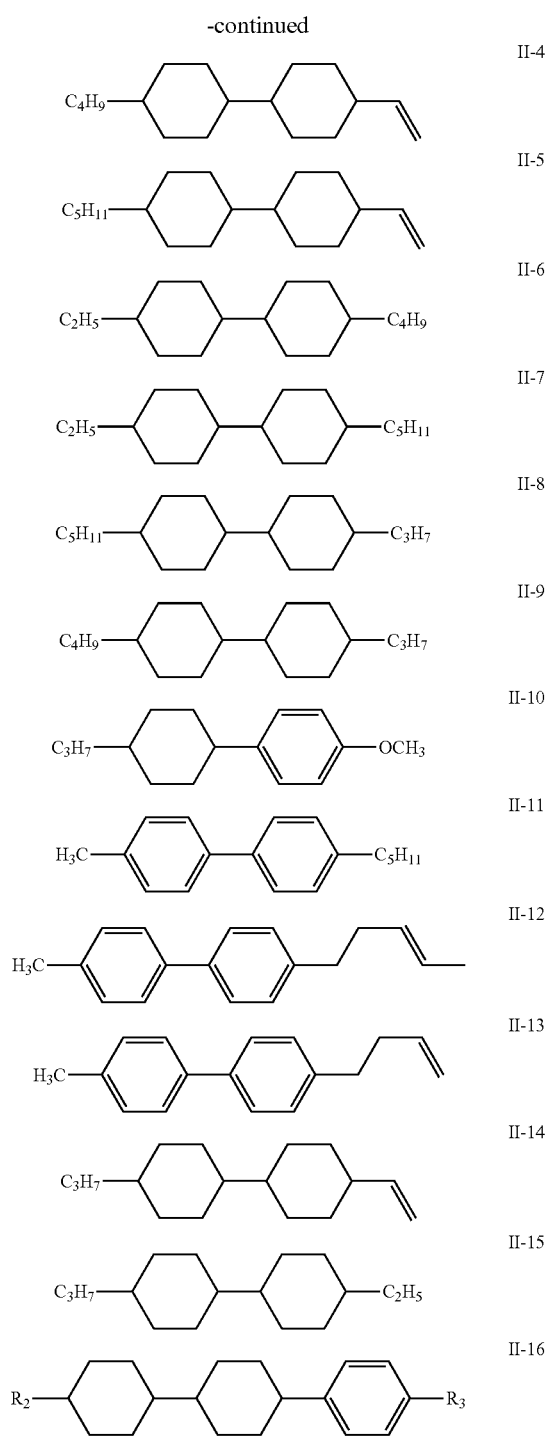

-continued

II-17

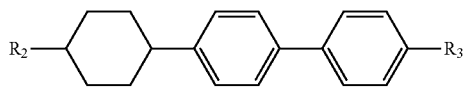

wherein $R_2$ and $R_3$ each independently represents an alkyl group having a carbon atom number of 1-10, an alkenyl group having a carbon atom number of 2-10, an alkoxy group having a carbon atom number of 1-10, and any one or more non-connected $CH_2$ in groups $R_2$ and $R_3$ may be substituted with cyclopentyl, cyclobutyl, cyclopropyl, or —O—.

5. The liquid crystal composition according to claim 3, wherein in said liquid crystal composition, the total content in mass percentage of the compounds represented by formula I is 1-40%, and the total content in mass percentage of the compounds represented by formula II is 5-65%.

6. The liquid crystal composition according to claim 3, wherein said liquid crystal composition further comprises one or more compounds represented by formula III

III

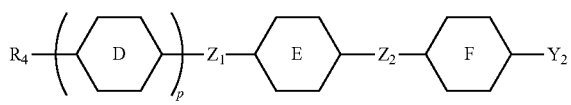

wherein $R_4$ represents an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or an fluoro-substituted alkenoxy group having a carbon atom number of 3-8; and any one or more $CH_2$ in group $R_4$ may be substituted with cyclopentyl, cyclobutyl or cyclopropyl;

each independently represents:

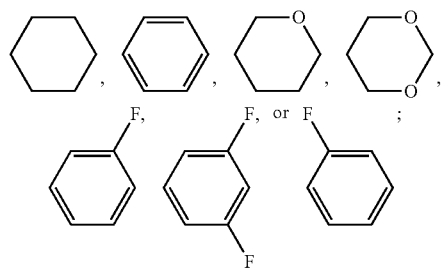

p represents 1, 2 or 3;
$Z_1$ and $Z_2$ each independently represent a single bond, —$CF_2O$—, —$CH_2CH_2$—, or —$CH_2O$—; and $Y_2$ represents F, a fluoro-substituted alkyl group having a carbon atom number of 1-5, a fluoro-substituted alkoxy group having a carbon atom number of 1-5, or an alkenyl group having a carbon atom number of 2-5.

7. The liquid crystal composition according to claim 6, wherein said one or more compounds represented by formula III are compounds of formulas III1 to III22

III1
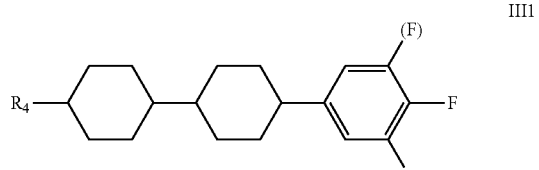

III2
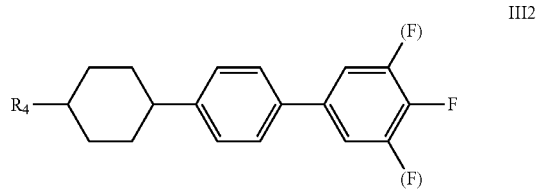

III3
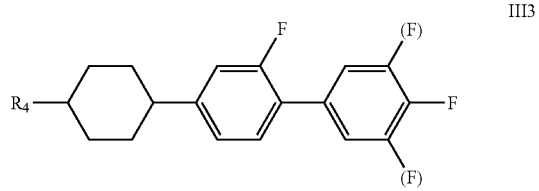

III4
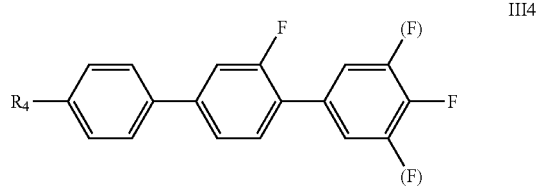

III5
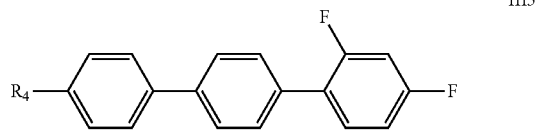

III6
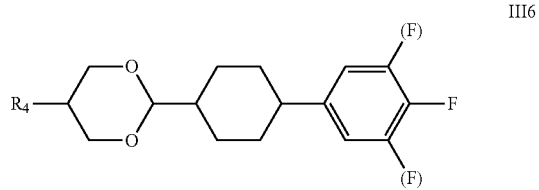

III7
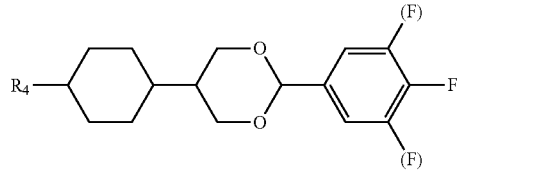

III8
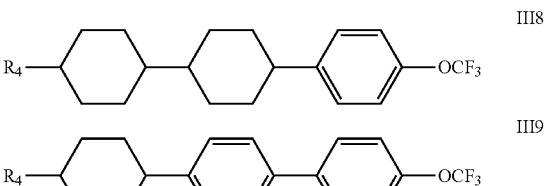

III9

III10

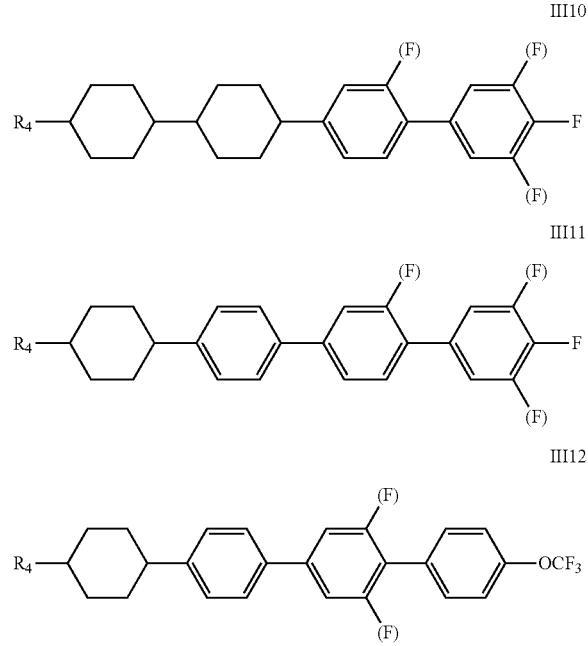

III18
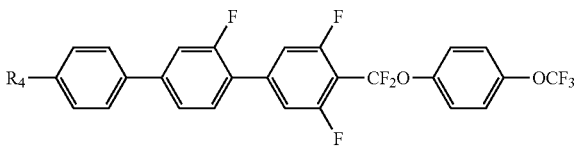

III19
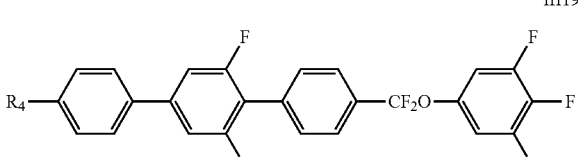

III20
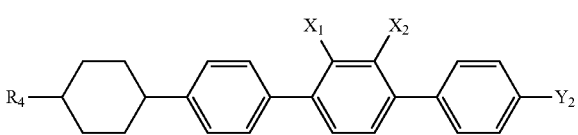

III21
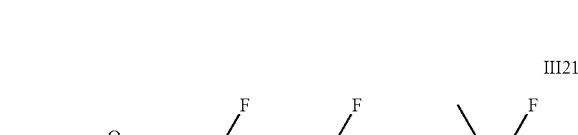

III22
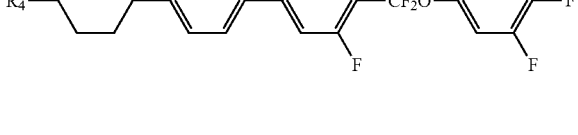

III14
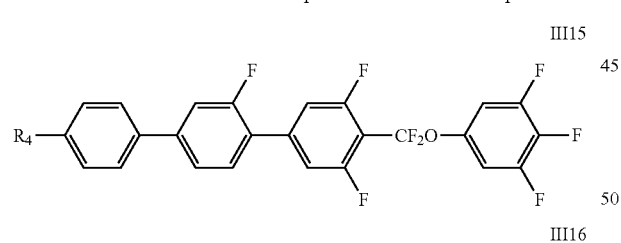

III15

III16
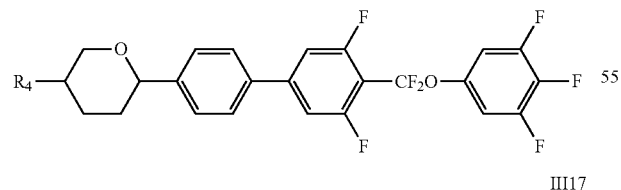

III17
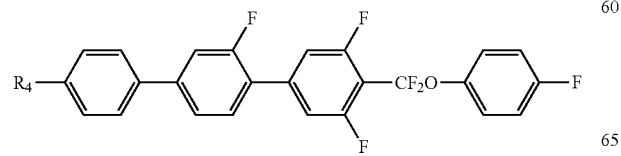

wherein $X_1$ and $X_2$ each independently represent H or F;

wherein each $R_4$ independently represents an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any $CH_2$ in group of $R_4$ may be substituted with cyclopentyl, cyclobutyl or cyclopropyl; (F) represents H or F; and $Y_2$ represents F, a fluoro-substituted alkyl group having a carbon atom number of 1-5, a fluoro-substituted alkoxy group having a carbon atom number of 1-5, or an alkenyl group having a carbon atom number of 2-5.

8. The liquid crystal composition according to claim 3, wherein said liquid crystal composition further comprises one or more compounds represented by formula IV

IV

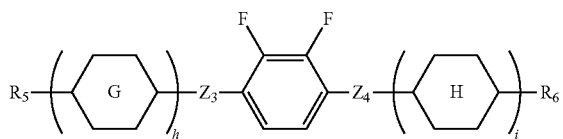

wherein $R_5$ and $R_6$ each independently represent an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any $CH_2$ in groups $R_5$ and $R_6$ may be substituted with cyclopentyl, cyclobutyl or cyclopropyl;

$Z_3$ and $Z_4$ each independently represent a single bond, —$CH_2CH_2$— or —$CH_2O$—;

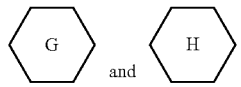

each independently represent

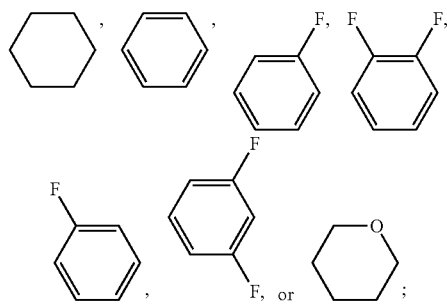

h represents 1, 2 or 3;
and i represents 0 or 1.

9. The liquid crystal composition according to claim 8, wherein the compound represented by formula IV is a compound represented by formulas IV1 to IV11

IV1
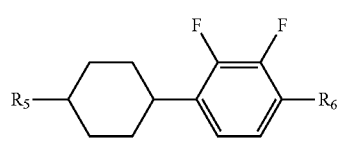

IV2
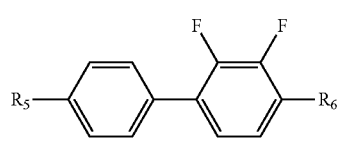

IV3
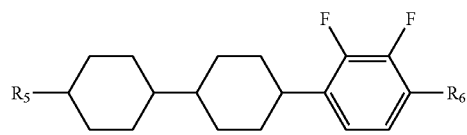

IV4
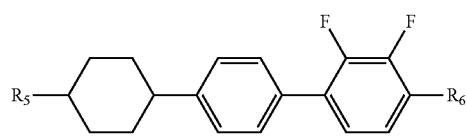

IV5
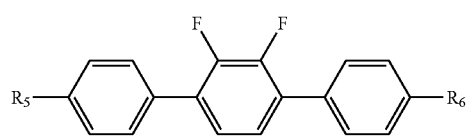

IV6
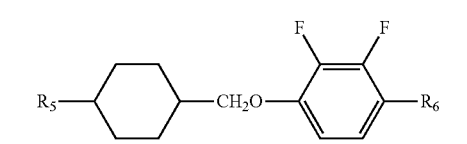

IV7
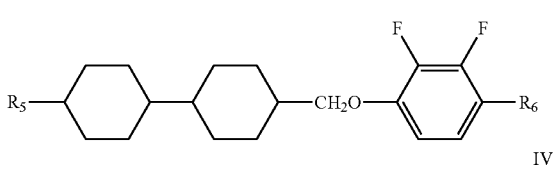

IV8
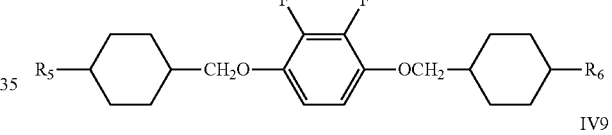

IV9
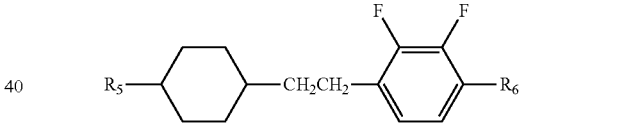

IV10
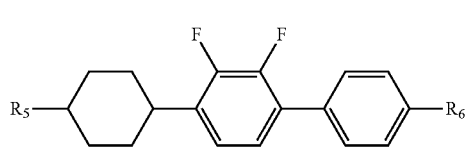

IV11 wherein $R_5$ and $R_6$ each independently represent an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any $CH_2$ in groups $R_5$ and $R_6$ may be substituted with cyclopentyl, cyclobutyl or cyclopropyl.

10. A liquid crystal display element or liquid crystal display comprising the liquid crystal compound of claim 1, wherein said liquid crystal display element or liquid crystal display is an active matrix display element or display or a passive matrix display element or display.

\* \* \* \* \*